United States Patent [19]

Lands et al.

[11] Patent Number: 4,675,281
[45] Date of Patent: Jun. 23, 1987

[54] QUANTIFICATION OF HYDROPEROXIDES USING PROSTAGLANDIN H SYNTHASE

[76] Inventors: William E. M. Lands, 901 S. Ashland #408; Richard J. Kulmacz, 901 S. Ashland #313, both of Chicago, Ill. 60607; Paul J. Marshall, 809 S. Marshfield, Chicago, Ill. 60612; Michael A. Warso, 6855 N. LeClaire, Skokie, Ill. 60077

[21] Appl. No.: 629,174

[22] Filed: Jul. 9, 1984

[51] Int. Cl.⁴ .................. C12Q 1/68; C12Q 1/26; C12Q 1/28; C12N 9/99

[52] U.S. Cl. ......................................... 435/4; 435/25; 435/28; 435/184

[58] Field of Search ................ 435/4, 184, 25, 28

[56] References Cited

U.S. PATENT DOCUMENTS

| | | | |
|---|---|---|---|
| 3,769,172 | 10/1973 | Bressler et al. | 435/12 |
| 4,368,261 | 1/1983 | Klose et al. | 435/15 |
| 4,368,262 | 1/1983 | Bucovaz et al. | 435/23 |

OTHER PUBLICATIONS

Yagi, Biochem. Med., 15, 212–216 (1976).
Perez, et al., Inflammation 4, 313–328 (1980).
Sato, et al., Biochem. Med., 21, 104–107 (1979).
Smith, et al., Biochem. Pharmacol., 31, 19–26 (1982).
Nishigaki, et al., Biochem. Med., 25, 373–378 (1981).
Nishigaki, et al., Biochem. Med., 24, 185–189 (1980).
Ottolenghi, et al., Arch. Biochem. Biophys., 79, 355–363 (1959).
Howes, et al., Resh. Comm. Chem. Path. Pharmacol., 2, 619–625 (1971).
Kulmacz, et al., Prostaglandins, 25, 531–540 (1983).
Lieberman et al., Science, 152, 213–214 (1966).
Dillard, et al., Lipids, 14, 989–995 (1979).
Graff, Meth. in Enzymology, 86, 386–392 (1982).
Hemler et al., J. Biol. Chem., 255, 6253–6261 (1980).
Asakawa, et al., *Lipids,* 15, 137–140 (1980).
Barber et al., Adv. Gerontol. Resh., 2, 355–397 (1967).
Bridges, et al., Ann. N.Y. Acad. Sci., 407, 42–63 (1983).

*Primary Examiner*—Sidney Marantz
*Assistant Examiner*—Patricia L. DeSantis

[57] ABSTRACT

A method of assessing certain disease conditions of body tissues and body fluids by the measurement of hydroperoxides therein; includes using the enzyme prostaglandin H synthase and observing the rate of enzyme-catalyzed oxygenation reaction, preferably with equipment such as a polarographic oxygen electrode that monitors the oxygen concentration. The presence of increased amounts of hydroperoxide cause a faster attainment of the optimal rate of enzyme-catalyzed oxygen consumption. This enzymic assay provides high sensitivity and selectivity for hydroperoxides. Cyanide may also be introduced to temper the reaction velocity to facilitate monitoring the enzyme reaction.

7 Claims, 3 Drawing Figures

13-HYDROPEROXY
LINOLEIC ACID (pmol)

QUANTIFICATION OF HYDROPEROXIDES USING PROSTAGLANDIN H SYNTHASE

TECHNICAL FIELD

This invention relates broadly to clinical reagents and assays measuring the chemical constituents and toxic agents in tissues and body fluids. In particular, this invention is in the subcategory of assays which employ enzymes as reagents. Enzyme-based assays are widely employed in clinical chemistry laboratories as reagents because enzymes are often highly specific for particular biological constituents. A few examples of this point are: uricase for the measurement of uric acid, glucose oxidase for the measurement of serum glucose concentration, and urease for the measurement of blood urea nitrogen.

The assay described herein permits a highly sensitive and selective direct measure of the quantity of hydroperoxides by a novel combination of reagents and procedures. The assay relates to the ways that the catalytic activity of an enzyme may depend upon an hydroperoxide. This dependency is rendered amenable to convenient measurement and quantitation by the combination of reagents and procedures. The invention described in this report is concerned with converting observations of rates of enzyme reactions into valid estimates of hydroperoxide levels. The requirement for lipid hydroperoxide has been estimated to be very low about 0.02 micromolar [Kulmacz and Lands (1983) Prostaglandin 25, 531]. The mildly inhibited enzyme can be used to measure quite low levels of hydroperoxide. The limit of sensitivity for 13-hydroperoxylinoleic acid was 6 pmoles. The assay based on the cyclooxygenase activity of prostaglandin H synthase responds directly to hydroperoxides whether they are in free or esterified forms, and thus avoids the problems associated with the generation of secondary compounds. A significant advantage of the enzymatic assay is that it can be used to estimate directly the level of hydroperoxide currently in a sample and not just the amount of hydroperoxide that was produced during an incubation period as is the case with assays utilizing fluorescence, luminescence or liberation of volatile hydrocarbons. Biological samples can be assayed directly or extracted into organic solvents for later analysis.

BACKGROUND ART

There is much current interest in lipid hydroperoxides in terms of evaluating their importance as a primary mechanism of tissue injury. Lipid hydroperoxides have been implicated in atherosclerosis, stroke, diabetes, emphysema due to exposure to pollution, cancer, drug toxicity, and aging. Ethanol, several xenobiotics and anthracycline antibiotics (which are currently employed in cancer chemotherapy) stimulate the generation of lipid hydroperoxides by tissues, and these peroxides may be related to the tissue damage caused by the formentioned stimulators. Research groups in Japan are now screening blood samples for hydroperoxides as an indicator of the extent of burn injury [I. Nishigaki et al. (1980) Biochem. Med. 24, 185–189] and in patients with diabetes [Y. Sato et al. (1979) Biochem. Med. 21, 104–107; I. Nishigaki et al. (1981) Biochem. Med. 25, 373–378.]. Lipid peroxidation has important pathophysiologic consequences for cells since some of the oxidized products can serve as highly potent biological agents [H. D. Perez, B. B. Heksler, and I. M. Goldstein (1980) Inflammation 4, 313] and others can be deleterious to cell membranes [J. W. Bridges, D. J. Benford, and S. A. Hubbard (1983) Ann. N.Y. Acad. Sci. 407, 42]. Small amounts of lipid hydroperoxides are known to acitvate prostaglandin H synthase (International Union of Biochemistry index EC1.14.99.1) in vitro [M. E. Hemler and W. E. M. Lands (1980) J. Biol. Chem. 255, 6253], although their precise role has been difficult to evaluate due to the lack of a sufficiently specific and sensitive analytical method.

Despite the emerging importance of lipid hydroperoxides, all of the currently available methods for the assay of lipid hydroperoxides in biological samples have serious limitations. The most widely used method, the thiobarbiturate assay [A. Ottolenghi (1959) Arch. Biochem. Biophys. 79, 355–363] actually measures a malondialdehyde-like substance, which results during the decomposition of the endoperoxides [B. Barber (1967) Adv. in Gerontol. Res. 2, 355–397]. Malondialdehyde may arise from sources other than lipid hydroperoxides, and whereas 0.1–0.5 $\mu M$ malondialdehyde may be detected, the efficiency of conversion of lipid hydroperoxides to malondialdehyde is only about 5% [T. Asakawa and S. Matsushita (1980) Lipids 15, 137–140]. Thus, the measurement of malondialdehyde is neither specific nor sensitive. A gas chromatography-based assay depends upon the decomposition of lipid hydroperoxides to form ethane and pentane [C. J. Dillard and A. L. Tappel (1979) Lipids 14, 989–995] or ethylene [M. Lieberman and P. Hochstein (1966) Science 152.213–214]. These gases can be measured accurately at low concentration, but this assay is limited to the estimation of the extent of lipid peroxidation occurring during an incubation period, and is not useful for the determination of the concentration of lipid hydroperoxides in, for example, blood plasma. Other assays utilize the chemiluminescence and fluorescence which accompany the process of lipid peroxidation. Not only is the basis for the light emission unclear [R.M. Howes and R.H. Steele (1971) Resh. Commun. Chem. Path. Pharmacol. 2,619–625], but these assays are only able to measure peroxides formed during the incubation period, and thus suffer from the same limitations as the measurement of volatile hydrocarbons in that they are not applicable to the determination of the level of lipid peroxide already in a sample.

DESCRIPTION OF PRIOR ART

The assay for hydroperoxides is based on our published indirect evidence for the requirement of the prostaglandin H synthase for lipid hydroperoxide at levels of approximately 0.02 micromolar to operate at 50 percent of its optimal activity [Kulmacz and Lands, (1983) Prostaglandins 25,531]. The existing assays for hydroperoxide lack the specificity and sensitivity to provide reliable determinations of lipid hydroperoxides.

The most sensitive thiobarbiturate assay procedure [K. Yagi (1976) Biochem. Med. 15, 212] under favorable conditions has a lowest detectable level of hydroperoxylinoleic acid on the order of 300 pmoles. The measurement of volatile hydrocarbons is a very indirect indicator of peroxides, and it has a detection limit of about 300 pmoles [M. T. Smith et al. (1982) Biochem. Pharmacol. 31, 19]. A new, sensitive analytical technique that is specific for the hydroperoxide group is needed to make reliable estimates of the actual level of hydroperoxides present in tissues.

DISCLOSURE

Cyclooxygenase activity of the prostaglandin H synthase is measured by measuring oxygen consumption with a polarographic oxygen electrode (Yellow Springs Instrument Co., Yellow Springs, OH.) as illustrted by the following procedures and examples. The incubation buffer (3 ml) for this assay contains 0.1M potassium phosphate (pH 7.2), 100 $\mu$M arachidonic acid, 1, mM phenol, and 2.5 mM sodium cyanide. The hydroperoxide was added immediately before the addition of the Prostaglandin H synthase to minimize the possibility of decomposition of the hydroperoxide. Prostaglandin H synthase (5 $\mu$g in 5 $\mu$l; 70 $\mu$moles of oxygen consumed/min) is injected into the reaction mixture. The change in the oxygen level with time is recorded, and the time required to reach the optimal velocity (lag time) is noted. The native enzyme did not exhibit a measureable response to added hydroperoxides, however we exploited the ability of sodium cyanide (0.5–15 millimolar) plus phenol (0.5–2 millimolar) to induce lags in cyclooxygenase velocity, and of added hydroperoxides to reduce these lags. The cyanide-treated system exhibited lag times (lag CONTROL) considerably longer than those of the untreated mixtures (lag UNINHIBITED) (see FIG. 1). Addition of hydroperoxides to the inhibited system decreases the lag time (lag SAMPLE) (FIG. 1). The enzyme response to added hydroperoxide is computed as a Fractional Activation in the following manner (FIG. 2):

Fractional Activation=(lag CONTROL−lag SAMPLE/lag CONTROL−Lag UNINHIBITED)

This treatment of the measured lag times provides an index of the response that is proportional to the amount of hydroperoxide added and normalizes the responses so that results from different assays can easily be compared (FIG. 3). To quantitate the hydroperoxide in a biological sample, the Fractional Activation is determined using an aliquot of the sample, and then compared to the Fractional Activations generated by a series of known amounts of standard hydroperoxide (FIG. 3). This comparison will then yield the amount of hydroperoxide present in the unknown sample.

Removal of contaminating hydroperoxides from the substrate arachidonic acid before addition to the reaction is necessary to obtain reproducibly long lag times with a given concentration of cyanide. In order to remove the contaminating hydroperoxides, the arachidonic acid (100 milligrams) is treated with sodium borohydride (15 milligrams) in 3 milliliters of toluene for 30 minutes at room temperature. The excess borohydride is then decomposed by the slow addition of 3 ml of water and 0.7 ml of citric acid (1 molar). After through mixing, the phases are allowed to separate. The organic layer is removed, washed with 1 ml of water, and the remaining traces of water removed by anhydrous sodium sulfate. The treated arachidonic acid is stored at 4° C. after the addition of 20 microliters of 10 millimolar butylated hydroxytoluene as an antioxidant.

The preparation of the lipid hydroperoxide standards is achieved by the method described by Graff [G. Graff (1982) Methods Enzymol. 86, 386–391].

APPLICABILITY

The procedure described in this application allows the measurement of lipid hydroperoxides present in biological samples in amounts as low as 20 to 30 pmoles. The probable concentrations of lipid hydroperoxides in normal and diseased tissue provide this amount of hydroperoxide in an aliquot of reasonable size. Thus, the assay can find considerable use in evaluating the levels of lipid hydroperoxides in a large number of physiological and pathological processes. This can be of utility in monitoring patient status in certain diseases or deficiency states during therapeutic procedures, and monitoring normal or disordered responses to nutritional supplies of polyunsaturated fatty acids.

As an example of the applicability of the enzymatic assay for hydroperoxides in a biological fluid, we have used the enzymatic assay thiobarbiturate assay to quantitate the amount of lipid hydroperoxides in normal human plasma. In the range of aliquots tested (50–125 $\mu$l), the Fractional Activations (0.15–0.45) obtained were highly reproducible and could be measured with good precision. The recovery efficiency of hydroperoxides added to the enzyme assay varied from 70% to 100%. The concentration values obtained by the enzyme assay for hydroperoxide concentration in plasma ranged from 0.26–0.73 $\mu$M with a mean of 0.50 $\mu$M.

As a further example of the applicability of the enzymatic assay for hydroperoxides, we examined the hydroperoxide levels in the blood plasma of patients with sepsis and adult respiratory distress syndrome (ARDS). Sepsis elicits a complex set of vascular responses that may be modulated by prostaglandins and leukotrienes. Bacterial endotoxin which is often released into the vasculature in septicemia which is often released into the vasculature in septicemia has been reported to activate leukocytes, increase the formation of lipid hydroperoxides, and enhance the pulmonary synthesis of the endoperoxide prostaglandin H. We monitored the lipid hydroperoxides in the plasma of patients by the enzymatic assay. The plasma lipid hydroperoxide level in 6 patients with sepsis or ARDS was 1.36 ($\pm$0.18) $\mu$M. There was a positive correlation between the plasma lipid hydroperoxide level and the cardiac index. Seven matched patients hospitalized for reasons other than ARDS or sepsis had plasma lipid hydroperoxide levels of 0.35($\pm$0.09) $\mu$M and 5 healthy volunteers had levels of 0.53($\pm$0.09) $\mu$M. Thus, the plasma hydroperoxides were significantly higher (P<0.01) in the patients with sepsis or ARDS. The hydroperoxide level in one patient exhibiting the symptoms of sepsis was 2.1 $\mu$M and it decreased to the normal range after partial recovery two weeks later. The higher level of plasma lipid hydroperoxides found in septic patients (1.36 $\mu$M) could be expected to cause an increased activation of cyclooxygenase and lipoxygenase and thereby increase the synthesis of prostaglandins and leukotrienes. The level is also in the range reported to destroy the prostacylcin synthase of endothelial cells. Thus, the elevated plasma hydroperoxides in patients with ARDS or sepsis may be important in mediating the complex vasular responses in these clinical conditions, and knowledge of the hydroperoxide levels should contribute to an evaluation of the therapy administered to these patients.

It is intended that all material contained in the above description shall be interpreted in an illustrative and not in a limiting sense.

Figure 1:
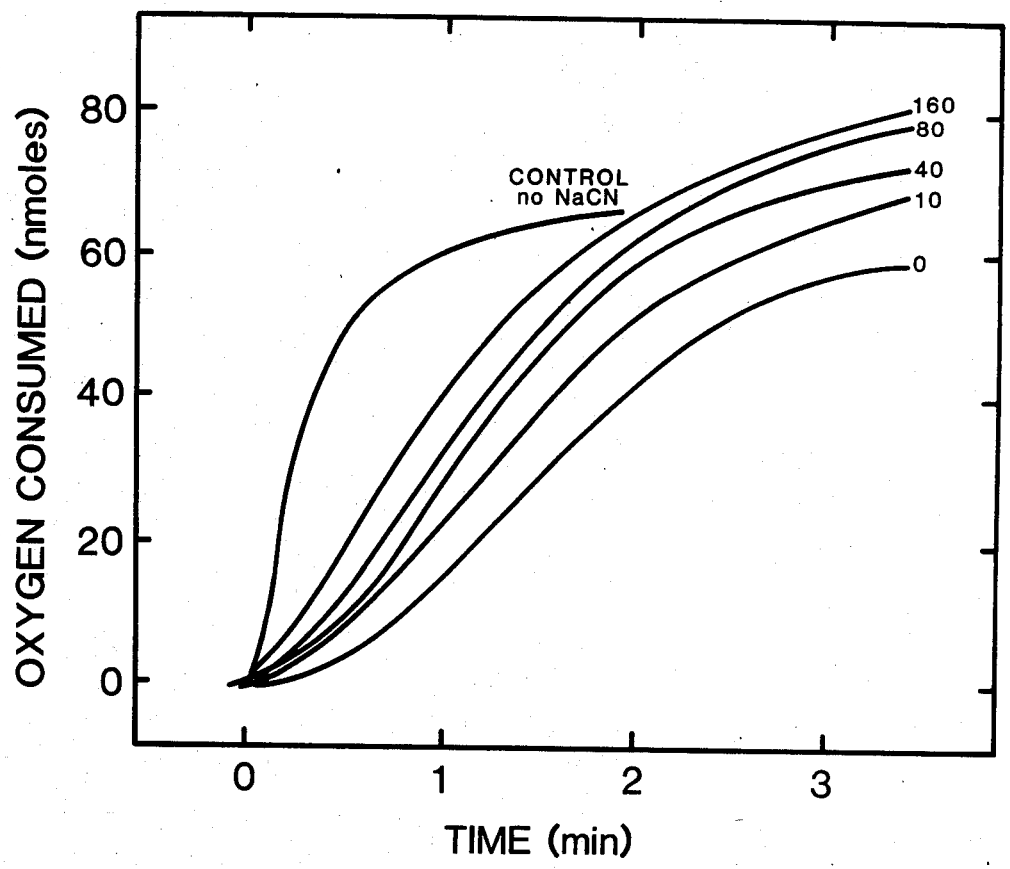
FIG. 1 is a representative set of results indicating the activation of cyanide/phenol-impaired prostaglandin H synthase by hydroperoxides. The enzyme was added to 3 ml of 0.1M potassium phosphate buffer (pH 7.2) containing 15 mM sodium cyanide, 1 mM phenol, 100 μM arachidonic acid, and the indicated nanomolar concentrations of 13-hydroperoxy linoleic acid. These tracings represent the decline in the oxygen concentration in solution as arachidonic acid was converted to prostaglandin $G_2$.
Figure 2:
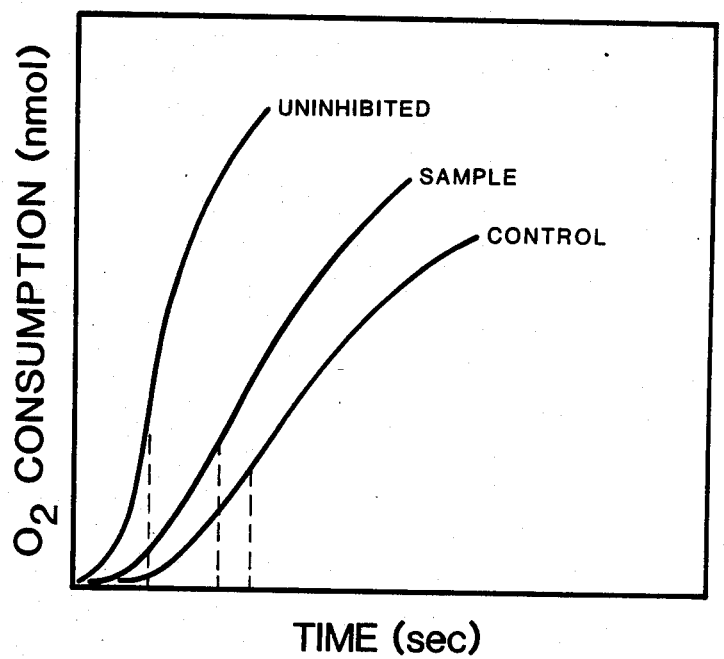
FIG. 2 is an illustration of the values used in calculating the Fractional Activation from the oxygen consumption tracings. The time for the reaction to attain optimal velocity (lag time) were determined by the time from enzyme addition to the inflection point of the oxygen consumption curve. Examples of the determinations are shown for the enzyme incubations (1) where no sodium cyanide was present (uninhibited), (2) where sodium cyanide and hydroperoxide were added (sample), and (3) where only sodium cyanide was added (control). The formula for calculation of Fractional Activation is also shown.
Figure 3:
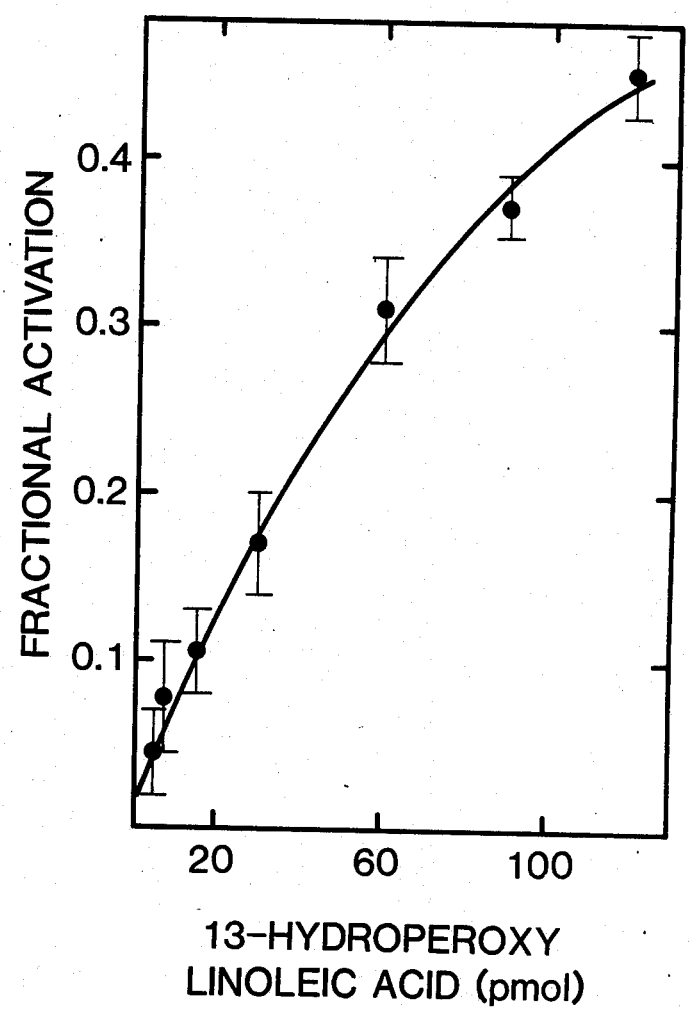
FIG. 3 is a representative standard curve relating the Fractional Activation to the 13-hydroperoxylinoleic acid concentration. Prostaglandin H synthase was added to 3 ml of 0.1M potassium phosphate (pH 7.2) that contained 1 mM phenol, 2.5 mM cyanide, 100 μM arachidonic acid, and varying amounts of hydroperoxide. The Fractional Activation was calculated for each individual incubation as described in the text and in the legend to FIG. 2. Each point, represents the mean ($\pm$SD) of six or more separate experiments. The curve is the line of best fit determined by the use of a second degree polynominal that was generated from the data.

We claim:

1. The method of quantifying the amount of hydroperoxide present in a biological sample as an indicator of the level of pathophysiology therein, including:
   i. establishing an incubation mixture that contains oxygen and arachidonic acid dissolved in a buffered aqueous solution,
   ii. adding to the incubation mixture portions of a sample to be tested,
   iii. adding a solution of prostaglandin H-synthase to catalyze the cyclooxygenation reaction; and
   iv. monitoring the progress of the enzyme-catalyzed reaction.

2. The method as described in claim 1, wherein the progress of the enzyme-catalyzed reaction is measured by monitoring the oxygen concentration.

3. The method as described in claim 2, wherein said monitoring is achieved by use of a polarographic oxygen electrode.

4. The method as set forth in claim 1, including the application of cyanide (0.5-15 millimolar) and phenol (0.5-2 millimolar) to step i to impair the reaction velocity of the enzyme and permit more precise monitoring of the reaction.

5. The method as set forth in claim 1, wherein the sample of step ii is a standard solution of hydroperoxide to calibrate the response of the assay system to a known amount of hydroperoxide.

6. The method of calculating the amount of hydroperoxide in a biological sample that was added to an assay system containing prostaglandin H synthase including the steps of:
   i. measuring the time needed for the assay system without added sample to reach optimal reaction velocity when not impaired with cyanide,
   ii. measuring the time needed for the assay system without added sample to reach optimal velocity when impaired with cyanide,
   iii. measuring the time needed for the assay system to reach optimal velocity when impaired with cyanide and when the added sample is a known amount of standard hydroperoxide,
   iv. calculating a Fractional Activation for each known amount of added standard hydroperoxide by computing the difference between the time value in step ii and the time value in step iii, and dividing this by the difference between the time value in step ii and the time value in step i,
   v. measuring the time needed for the assay system to reach optimal velocity when impaired with cyanide and a biological sample has been added,
   vi. calculating a Fractional Activation for each biological sample by computing the difference between the time value in step ii and the time value in step v, and dividing this by the difference between the time value in step ii and the time value in step i; and
   vii. comparing the Fractional Activation value of assay mixtures of the biological sample to those for the known standard hydroperoxide samples to estimate the content of hydroperoxide in the biological sample.

7. In a procedure intended to quantitate the amount of hydroperoxide in a biological sample by way of an assay so as to indicate the degree of pathophysiology therein, the improvement comprising the use of the enzyme prostaglandin H synthase to quantitate the amount of hydroperoxide in a sample added to the assay system by way of its cyclooxygenase activity.

* * * * *